(12) United States Patent
Roufs et al.

(10) Patent No.: US 6,989,161 B2
(45) Date of Patent: Jan. 24, 2006

(54) PHYTONUTRIENT NUTRITIONAL SUPPLEMENT

(75) Inventors: James B. Roufs, Long Beach, CA (US); Chioma J. Ikonte, Buena Park, CA (US); Mary A. Murray, Irvine, CA (US); Audra J. Davies, Long Beach, CA (US)

(73) Assignee: Access Business Group International LLC, Ada, MI (US)

( * ) Notice: Subject to any disclaimer, the term of this patent is extended or adjusted under 35 U.S.C. 154(b) by 340 days.

(21) Appl. No.: 10/360,789

(22) Filed: May 7, 2002

(65) Prior Publication Data

US 2004/0131656 A1      Jul. 8, 2004

Related U.S. Application Data

(63) Continuation-in-part of application No. 09/878,377, filed on Jun. 12, 2001, now Pat. No. 6,511,675.

(60) Provisional application No. 60/210,746, filed on Jun. 12, 2000.

(51) Int. Cl.
  *A61K 35/78* (2006.01)
  *A61K 47/00* (2006.01)
  *A01N 43/04* (2006.01)
  *A01N 43/16* (2006.01)

(52) U.S. Cl. .................. 424/725; 424/439; 514/27; 514/456

(58) Field of Classification Search ............... 424/725, 424/442, 439; 514/27, 456
  See application file for complete search history.

(56) References Cited

U.S. PATENT DOCUMENTS

| | | | |
|---|---|---|---|
| 5,231,193 A * | 7/1993 | Mizusawa et al. ......... 549/299 |
| 5,356,636 A | 10/1994 | Schneider et al. | |
| 5,401,502 A | 3/1995 | Wunderlich et al. | |
| 5,514,382 A | 5/1996 | Sultenfuss | |
| 5,578,336 A | 11/1996 | Monte | |
| 5,612,039 A | 3/1997 | Policappelli et al. | |
| 5,654,011 A | 8/1997 | Jackson et al. | |
| 5,686,108 A | 11/1997 | Pusateri et al. | |
| 5,770,217 A | 6/1998 | Kutilek, III et al. | |
| 5,807,586 A | 9/1998 | Jackson et al. | |
| 5,827,900 A * | 10/1998 | Levy et al. ................. 514/762 |
| 5,830,887 A | 11/1998 | Kelly | |
| 5,840,278 A | 11/1998 | Coleman | |
| 5,882,646 A | 3/1999 | Pusateri et al. | |
| 5,904,924 A | 5/1999 | Gaynor et al. | |
| 5,948,443 A | 9/1999 | Riley et al. | |
| 5,955,102 A | 9/1999 | Gorenbein et al. | |
| 5,972,985 A | 10/1999 | Thomas et al. | |
| 5,976,548 A | 11/1999 | Hsia et al. | |
| 5,976,568 A | 11/1999 | Riley | |
| 5,985,338 A | 11/1999 | Suh et al. | |
| 6,022,901 A | 2/2000 | Goodman | |
| 6,075,058 A * | 6/2000 | Handelman ................. 514/729 |
| 6,203,818 B1 | 3/2001 | Vester | |
| 6,228,358 B1 | 5/2001 | Toba et al. | |
| 6,261,598 B1 | 7/2001 | Runge et al. | |
| 6,299,925 B1 * | 10/2001 | Xiong et al. ................ 426/597 |
| 6,562,866 B1 * | 5/2003 | Bok et al. ................... 514/456 |
| 2002/0055620 A1 | 5/2002 | Aga et al. | |

FOREIGN PATENT DOCUMENTS

| | | | |
|---|---|---|---|
| EP | 402049 | * | 1/1990 |
| EP | 0906761 | | 10/1998 |
| JP | 2000078956 | * | 3/2000 |
| WO | WO 0045829 | | 2/1999 |
| WO | WO 0064282 | | 4/2000 |

* cited by examiner

Primary Examiner—Christopher R Tate
Assistant Examiner—Randall Winston
(74) Attorney, Agent, or Firm—Warner Norcross & Judd LLP

(57) ABSTRACT

A composition and method for correcting a dietary phytonutrient deficiency. The composition includes one or more of the following phytonutrients: lutein, lycopene, epigallocatechin gallate (EGCG), ellagic acid, hesperidin and quercetin. Dietary phytonutrient deficiencies are corrected by administration of these phytonutrients in amounts equal or greater than the amounts of these phytonutrients present in recommended daily servings of fruits and vegetables.

12 Claims, No Drawings

PHYTONUTRIENT NUTRITIONAL SUPPLEMENT

This is a continuation-in-part of U.S. patent application Ser. No. 09/878,377, filed Jun. 12, 2001, now U.S. patent No. 6,511,675, which is hereby incorporated by reference, and which claims benefit of U.S. Provisional Application No. 60/210,746, filed Jun. 12, 2000.

BACKGROUND

The present invention relates to a composition and method for correcting a diet-induced inadequacy of phytonutrients.

In the past decade, it has been observed that a significant portion of the human population has adopted undesirable and unhealthy eating habits. For example, much of the population of the United States fails to intake the quantity and variety of food adequate to meet U.S. Recommended Daily Dietary Allowances. Only 22% of subjects in a National Cancer Institute Study consume the recommended daily number of dietary servings of fruits and vegetables, even though information regarding the recommended servings is well published by many health organizations.

Most health guidelines recommend that each person consume at least five to nine servings of fruit and vegetables per day. *Dietary Guidelines for Californians*, The California Daily Food Guide, California Department of Health Services (1990). Some researchers suggest that a target of 400 grams of fruits and vegetables is a sensible goal for the optimal quantity to be consumed daily. In terms of variety, researchers recommend that persons should eat at least three different colors of fruits and vegetables per day.

Coupled to the observation of inadequate intake of fruits and vegetables is a verified conclusion that the diet of a typical U.S. citizen, a "western diet," is deficient in phytonutrients. Phytonutrients generally refer to plant-derived compounds which, when taken daily, provide improved cardiovascular and bone health, improved antioxidant profile, decreased free radical damage and overall enhancement of the body's immunological system. The difference between the recommended amount of phytonutrients and the amount ingested in a typical western diet is referred to as a gap. The following table represents a gap analysis for two phytonutrients, lutein and lycopene. Lutein is a phytonutrient found in green leafy vegetables, such as spinach. Lycopene is a phytonutrient present in tomatoes.

| Phytonutrient | Recommended | Typical U.S. Diet | Gap |
|---|---|---|---|
| Lutein | 19.5–25.6 mg. | 1.8 mg. | 20.75 mg. |
| Lycopene | 4.2–10 mg. | 2.2 mg. | 2–7.8 mg. |

This gap, which is even more pronounced for other phytonutrients, has been linked to significant health implications. The ingestion of phytonutrient-rich fruits and vegetables has been shown to decrease the occurrence of several chronic degenerative diseases, such as cancer, cardiovascular disease, chronic macular degeneration, and delay on the onset and/or slowing of the progression of coronary heart disease. For example, in cell culture studies, lycopene's ability to inhibit breast cancer tumors was compared to that of alpha and beta-carotene. The cell cultures that were enhanced with lycopene showed that it inhibited the growth of breast cancer cells and that the alpha and beta-carotene were far less effective than lycopene in inhibiting the cell growth. Levy, J. et al, *Lycopene is a More Potent Inhibitor of Human Cancer Cell Proliferation Than Either A-Carotene or Beta-Carotene*, Nutrition Cancer, 24:257–266 (1995).

Another study found that an increased intake of fresh tomatoes (a major source of lycopene) was associated with a pattern of protection for all sites of digestive tract cancer. Stall, W. et al., *Lycopene: A Biologically Important Carotenoid for Humans?* Arc. Biochem. Biophys., 336:1–9 (1996). In a study of 41,837 post-menopausal women, researchers investigated the association of fruit and vegetable consumption with lung cancer risk. The risk of lung cancer was discovered to be approximately halved when the consumption of fruits and vegetables increased from twenty-four or less servings to an excess of forty-eight servings per week. Similarly, the risk of lung cancer was approximately halved when the consumption of green leafy vegetables including spinach sources increased from one or fewer servings to six or more servings per week. Steinmetz, K., et al, *Vegetables, Fruit and Lung Cancer in the Iowa Women's Health Study*, Cancer Research, 53:536–543 (1993).

The typical western diet is significantly deficient in beneficial phytonutrients found in fruits and vegetables due to inadequate consumption and imbalanced dietary intake. Therefore, an opportunity exists to correct dietary deficiencies in these phytonutrients.

SUMMARY OF THE INVENTION

The aforementioned problems are overcome in the present invention in which a phytonutrient nutritional supplement includes a unique combination of phytonutrients that can reduce or eliminate the dietary gap that exists between an optimal diet and a conventional western diet. A preferred supplement contains, but is not limited to, at least three of the following phytonutrients: lutein, lycopene, epigall-catechin-gallate (EGCG), ellagic acid, hesperidin and quercetin.

In a more preferred embodiment, the supplement bridges the gap in actual phytonutrient intake and a healthy phytonutrient intake by providing at least three specific phytonutrients in amounts equivalent to the amount in multiple servings of fruits and vegetables. In an even more preferred embodiment, the supplement provides an amount of lutein, lycopene, EGCG, ellagic acid, hesperidin and quercetin that is equivalent to those amounts present in ten or more servings of fruits and vegetables, as recommended to meet U.S. Recommended Dietary Allowances.

In another aspect of the present invention, a method is provided for correcting an inadequacy of phytonutrients by administering a dietary supplement to a subject known to have a phytonutrient deficiency, such as diet-induced phytonutrient deficiency, wherein the supplement contains an effective amount of at least three of the following phytonutrients: lutein, lycopene, EGCG, ellagic acid, hesperidin and quercetin.

In a third aspect of the present invention, a method is provided for improving the antioxidant profile of a subject having a poor antioxidant profile by administering a dietary supplement containing an effective amount of at least three of the following phytonutrients: lutein, lycopene, EGCG, ellagic acid, hesperidin and quercetin.

In a fourth aspect of the present invention, there is provided a method for decreasing free radical damage in the human body by administering a dietary supplement to a subject in need thereof, wherein the supplement contains an effective amount of at least three of the following phytonutrients: lutein, lycopene, EGCG, ellagic acid, hesperidin and quercetin, and possibly other phytonutrients.

In another aspect of the present invention, there is provided a method for improving cardiovascular and bone health through the administration of a dietary supplement to a subject in need thereof, wherein the supplement includes an effective amount of at least three of the following phytonutrients: lutein, lycopene, EGCG, ellagic acid, hesperidin and quercetin.

In yet another aspect of the present invention, there is provided a method for enhancing the immunological response of the human body through the administration of a dietary supplement containing an effective amount of at least three of the following phytonutrients: lutein, lycopene, EGCG, ellagic acid, hesperidin and quercetin.

Administration of the phytonutrient supplement of this invention provides substantial health benefits. For example, the present invention provides phytonutrients that have been shown to improve or at least support the health of people who consume a nutritionally and phytonutriently deficient diet. Further, the phytonutrient supplement of the present invention replenishes phytonutrient levels that have deteriorated as a result an inadequate diets to levels associated with risks of certain degenerative diseased states. Additionally, this phytonutrient supplement improves antioxidant and nutrient status, minimizes free radical damages that typically occur as the result of the normal aging processes and exposure to environmental stresses and improves the status of specific biomarkers indicative of optimal health, for example, elliptic oxidation byproducts, antioxidant measures and glutathione peroxidase.

These and other objects, advantages and features of the invention will be more readily understood and appreciated by reference to the detailed description of the invention and the drawings.

DETAILED DESCRIPTION OF THE INVENTION

A phytonutrient dietary supplement in accordance with a preferred embodiment of the invention includes at least three of the following phytonutrients: lutein, lycopene, epigallocatechin gallate (EGCG), ellagic acid, hesperidin and quercetin. A preferred method for correcting a diet-induced deficiency of phytonutrients in accordance with the invention includes administering a dietary supplement to a subject known to have a phytonutrient deficiency, for example, a diet-induced phytonutrient deficiency, wherein the supplement contains at least three of the following phytonutrients: lutein, lycopene, EGCG, ellagic acid, hesperidin and quercetin.

I. Phytonutrient Supplement Composition

In the preferred embodiment, a daily dosage of the phytonutrient dietary supplement includes amounts of lutein, lycopene, EGCG, ellagic acid, quercetin and hesperidin equivalent to the amounts of these phytonutrients in about 1 to about 10 servings of fruits and vegetables. The daily dosage of the phytonutrient supplement also contains the antioxidant potential found in about 1 to about 25 servings, and more preferably in about 1 to about 50 servings of various fruits and vegetables, based on phytonutrients.

The phytonutrients present in the invention may be obtained from multiple plant materials, including but not limited to the following: spinach, tomatoes, apples, raspberries, oranges, swiss chard, okra, pomegranate, quercetin, oak, marigold, grapefruit, strawberries, blueberries, elderberries, rosemary, broccoli, carrots and acerola cherry.

The amount or fruit and vegetable equivalency present in a daily dosage of a preferred phytonutrient supplement containing three or more of the following: lutein, lycopene, quercetin, ellagic acid, hesperidin and EGCG will now be described.

The amount of lutein present preferably is equivalent to the amount of lutein present in about 1 to about 10 servings of either raw spinach or raw broccoli. One serving of either is about one cup of those vegetables. The amount of lutein present in about 1 to about 10 servings of raw spinach is about 1.9 to about 20 milligrams (mg). More preferably, the lutein content in a daily dosage of the phytonutrient supplement is about 3 mg to about 10 mg and more preferably, about 6 mg, which is equivalent to about two servings of raw spinach. Another source of lutein used to obtain the above amounts is marigold extract.

The amount of lycopene present preferably is equal to the amount of lycopene present in about 1 to about 7 servings of tomato. One serving of tomato is one tomato. The amount of lycopene present in about 1 to about 7 servings of tomato is about 3 to about 20 mg. More preferably, the lycopene present the daily dosage of the phytonutrient supplement is about 2 to about 10 mg and most preferably, about 3 mg of lycopene.

The amount of quercetin in the daily dosage of the phytonutrient supplement is preferably equivalent to about 1 to about 10 apples. A serving of apple is equal to about one large apple. This number of servings of apples includes from about 30 mg to about 300 mg quercetin. More preferably, the daily dosage of the phytonutrient supplement includes an amount of quercetin in about 3 to 5 large apples or from about 90 mg to about 150 mg of quercetin and, most preferably, an amount of quercetin in about 5 apples or about 150 mg of quercetin.

The ellagic acid is present in the preferred daily dosage of phytonutrient supplement in an amount equivalent to about 1 to about 5 servings of strawberries and/or raspberries. One serving of these fruits is equal to about one cup. About 1 to about 5 servings of these fruits include about 20 mg to about 150 mg of ellagic acid. More preferably, ellagic acid in the daily dosage of phytonutrient supplement is present in an amount equivalent to about 1.5 servings of raspberries or strawberries, or about 40 mg of ellagic acid. The ellagic acid may be obtained from various sources, including pomegranate, raspberry and/or strawberry extracts or concentrates or the fruits directly.

In a preferred daily dosage of the phytonutrient supplement, hesperidin is present in an amount equivalent to about 1 to about 10 servings of oranges or about 15 mg to about 225 mg of hesperidin. One serving is one large orange. More preferably, hesperidin is present in an amount of about 60 mg. Optionally, the hesperidin may be provided from orange extract equivalent to the desired number of servings of oranges.

The EGCG present in a preferred daily dosage of the phytonutrient supplement includes an amount of EGCG found in about 1 to about 5 cups of green tea, or about 25 mg to about 150 mg of EGCG. More preferably, the EGCG present in the daily dosage is about 2.5 servings of green tea (or 2.5 cups) or about 90 mg of EGCG. Most preferably, the 90 mg of EGCG is provided via a green tea extract that also provides a minimum of 95% potency polyphenols, 75% potency catechins and 40% EGCG.

Additional specialty ingredients may be included in the phytonutrient supplement, and include one or more of the following: blueberry, elderberry, rosemary, broccoli, spinach, carrot and acerola cherry. These additional ingredients may be added to the phytonutrient supplement in any desired form, for example, powders, extracts, dehydrates, pulps and concentrates.

Optionally, the phytonutrient supplement may include a pharmaceutically acceptable excipient, for example, croscarmellose sodium, maltodextrin, silicified microcrystalline cellulose, silicon dioxide, stearic acid, hydroxyl propyl methyl cellulose (HPMC), lactose, glucose, sucrose, corn starch, potato starch, cellulose acetate, ethyl cellulose and the like. Dilutents and other additives such as one or more pharmaceutically acceptable binding agents, fillers, supports, thickening agents, taste-improving agents, coloring agents, preservatives, stabilizers, regulators, emulsifiers or mixtures thereof, also may be used depending on the form of the composition employed.

Preferably, the phytonutrient supplement is substantially free from additional vitamins or minerals. As desired, however, these ingredients may be added.

Table I illustrates the active phytonutrient contents of the phytonutrient supplement of one exemplary embodiment of the invention. The dosages may be altered without departing from the spirit and scope of the invention.

TABLE I

Active Phytonutrients Present in Daily Dosage of Preferred Supplement

| Phytonutrient | Amounts Per Day in mg. |
|---|---|
| Lutein | 6 |
| Lycopene | 3.1 |
| EGCG | 90 |
| Ellagic Acid | 40 |
| Hesperidin | 60 |
| Quercetin | 150 |

A specific embodiment of the phytonutrient supplement of the present invention is illustrated in following example.

EXAMPLE 1

Two tablets are prepared that provide active phytonutrients and specialty ingredients. The unit "amount per two tablets per day" in the following Dosage Table, Table II, means that the amount recited is given in the number of milligrams in two tablets. Two tablets for this example comprise the daily dosage of the phytonutrient supplement. Ingredients for which no amounts are given are standard in the art and those amounts may be varied as desired. The ingredients which include a "% potency" indicates that an extract with a certain potency is used. For example, "10% potency" means that per 100 grams of material, 10 grams is the amount of the indicated phytonutrient present in that extract. "Minimum" indicates the minimum amount of the active phytonutrient present in the ingredient.

TABLE II

Dosage Table

| Ingredients | Ingredient Amounts 2 Tablets/Day | Active Phytonutrient Ingredient Amounts 2 Tablets/Day |
|---|---|---|
| Croscarmellose Sodium | — | — |
| Maltodextrin, M-510 | — | — |
| NUTRILITE Phytonutrient Concentrate (see below) | 110 | n/a |

TABLE II-continued

Dosage Table

| Ingredients | Ingredient Amounts 2 Tablets/Day | Active Phytonutrient Ingredient Amounts 2 Tablets/Day |
|---|---|---|
| Lutein Ester Beadlets (10% potency) | 12 | 6 |
| Silicified Microcrystalline Cellulose | — | — |
| Natural Lycopene Beadlets | 3.1 | 3.1 |
| Silicon Dioxide | — | — |
| Stearic Acid, Powder, Vegetable | — | — |
| Aqueous H.P.M.C. (5 centipoise) | — | — |
| Green Tea Extract (minimum of 40% EGCG, minimum 95% polyphenols and minimum 75% catechins) | 225 | 90 |
| Pomegranate Extract (minimum 40% ellagic acid) | 100 | 40 |
| Orange Extract (minimum of 80% hesperidin) | 75 | 60 |
| Quercetin (minimum of 90% quercetin) | 166.7 | 150 |

The NUTRILITE Phytonutrient Concentrate in Table II above, available from Access Business Group LLC of Ada, Mich., United States, includes ingredients including at least two of the following: blueberry powder, elderberry extract, rosemary extract, broccoli dehydrate, spinach powder, carrot pulp powder and acerola cherry concentrate in varying amounts to equal a combined amount of 110 mg per daily dosage.

The two tablets, when both administered in a single day, contribute to filling the gap in phytonutrients that is present in the typical western diet.

In the above tables, the overages of the recited ingredients may be added to guarantee that the listed amounts are actually present in the amount recited after the finished product is stored for a number of months. Green tea extract, pomegranate extract, orange extract and quercetin may include overages of 10%, 10%, 50% and 15%, respectively, to guarantee the amounts of active ingredients recited in Table II. For example, in the ingredients listed in Table II, green tea extract may be 247.5 mg; pomegranate extract may be 110 mg; orange extract may be 112.5 mg; and quercetin may be 191.7 mg.

Optionally, additional phytonutrients may be added to the ingredients in Table I. For example, resveratrol, in amounts with a lower limit of 3 mg, preferably 6 mg and more preferably 12 mg to amounts with upper limits of 25 mg, preferably 18 mg and more preferably 14 mg, may be added. Sources of resveratrol include grape seed, grape skin and polygonum cuspidatum extract. Sulfurophane also may be added to the ingredients in amounts with a lower limit of 50 mg, preferably 75 mg and more preferably 150 mg, and to amounts with upper limits of 300 mg, preferably 200 mg, and more preferably 155 mg. Suitable sources of sulfurophane are broccoli sprouts extract with minimum 0.4% potency, or from broccoli sprouts directly.

II. Method of Manufacturing the Phytonutrient Supplement

A preferred method of manufacturing tablets including the preferred phytonutrient supplement and ingredients as illustrated in Example 1 will now be described. It will be appreciated that other administration mediums, such as gel tabs, capsules, liquid and sustained release formulations can be formulated and prepared according to manufacturing techniques well known in the pharmaceutical industry.

In a preferred manufacturing process, the green tea extract, pomegranate extract, orange extract and quercetin in the amounts recited in Table II above are added to silicone dioxide and placed in a polybag and blended until uniformly and homogeneously mixed. This resultant blend is referred to as the Pre-Blend A. Pre-Blend A is placed in a Patterson Kelley (P.K.) 100 blender available from Patterson-Kelley Co., East Stroudsburg, Pa., USA. The following ingredients in the order listed are then passed through a Sweco separator equipped with a 20-mesh screen available from Sweco, Inc. of Florence, Ky., USA, directly into the PK. 100 blender: lutein ester beadlets (10% potency); natural lycopene beadlets, NUTRILITE Phytonutrient Concentrate (see Table III), dextrose, croscarmellose sodium, and silicified microcrystalline cellulose. Optionally, an overage of synthetic lycopene of 5% potency may be added to the formulation to provide overage protection of the natural lycopene beadlets. The resultant composition is blended in the P.K. 100 blender for 15 minutes.

A vegetable-based stearic acid powder is then passed through the Sweco separator directly into the P.K. 100 blender. The resultant mixture is blended for an additional five minutes. The resulting mixture is discharged into totes or super sacks, compressed punched into tablets by conventional means. An acceptable range weight for each individual tablet is from about 750 mg to 900 mg, more preferably from about 800 mg to about 880 mg and most preferably about 860 mg.

The phytonutrient supplement of Example I is preferably administered orally but may be administered parenterally. In the oral administration, the daily dosage is administered as two separate tablets that may be taken together or at different times during a day. However, the selection of other administration forms and unit dosages may be selected as desired.

Other suitable forms for the phytonutrient supplement for oral or parenteral administration include gel tabs, capsules, lozenges, strips, granules, solutions and suspensions, that contain unit doses of the supplement for administration once or several times a day. The phytonutrient dietary supplement of the invention may also be formulated with other foods or liquids to provide pre-measured supplemental foods, such as single serving bars, for example.

III. Oxygen Radical Absorbtion Capacity

Tablets manufactured including the preferred phytonutrients and ingredients of Example 1 exhibited an extremely high oxygen radical absorbtion capacity (ORAC). Preferred levels of ORAC of the present invention have an ORAC value of greater than 3000, preferably greater than 3500, more preferably greater than 5000 in a daily dosage of the phytonutrient supplement.

The ORAC values of resultant tablets comprising the ingredients of Example 1 were analyzed to determine the antioxidant protection afforded by a sample of the formulation against peroxyl free radicals. The antioxidant response obtained by the ORAC evaluation method used in the present invention was normalized to that of Trolox, and is expressed as micromoles Trolox equivalents per tablet for each sample. The preferred method, $ORAC_{FL}$ uses the fluorescent dye fluorescein to monitor antioxidant protection. This method is well known and will not be discussed in detail here.

In the formula of Example 1, individual tablets including the listed ingredients and having a tablet weight of 839 mg had an $ORAC_{FL}$ value of 3767±272.

Accordingly, the phytonutrient dietary supplement of the invention not only provides many beneficial phytonutrients, but also provides them in such a way to provide enhanced antioxidant protection as indicated by high ORAC values.

The above descriptions are those of the preferred embodiments of the invention. Various alterations and changes can be made without departing from the spirit and broader aspects of the invention as defined in the appended claims, which are to be interpreted in accordance with the principles of patent law including the doctrine of equivalents. Any references to claim elements in the singular, for example, using the articles "a," "an," "the," or "said," is not to be construed as limiting the element to the singular.

The invention claimed is:

1. A dietary supplement comprising the phytonutrients: lutein, lycopene, quercetin, ellagic acid, hesperidin and epigallocatechin gallate, each phytonutrient present in an amount sufficient to correct a dietary deficiency of that phytonutrient, wherein the combination of ingredients provides an oxygen radical absorption capacity of at least 3000.

2. The dietary supplement of claim 1 wherein the lycopene is present in an amount of about 3 mg to about 20 mg.

3. The dietary supplement of claim 2 wherein the lutein is present in an amount of about 1.9 mg to about 20 mg.

4. The dietary supplement of claim 1 wherein the phytonutrients are obtained from a plurality of plant materials selected from the group consisting of spinach, tomatoes, apples, raspberries, oranges, swiss chard, okra, pomegranate, oak, marigold, grapefruit, strawberries, blueberries, elderberries, rosemary, broccoli, carrots and acerola cherries.

5. The dietary supplement of claim 1 wherein the ellagic acid is present in an amount equivalent to the amount of ellagic acid in about 1 to about 5 servings of at least one of strawberries and raspberries.

6. The dietary supplement of claim 1 wherein the lutein is present in an amount equivalent to the amount of lutein present in about 1 to about 10 servings of at least one of spinach and broccoli.

7. The dietary supplement of claim 1 wherein the lycopene is present in an amount equivalent to the amount of lycopene present in about 1 to about 7 servings of tomato.

8. The dietary supplement of claim 1 wherein the quercetin is present in an amount equivalent to the amount of quercetin present in about 1 to about 10 apples.

9. The dietary supplement of claim 1 wherein the hesperidin is present in an amount equivalent to the amount of hesperidin present in about 1 to about 10 servings of oranges.

10. The dietary supplement of claim 1 wherein the epigallocatechin gallate is present in an amount equivalent to the amount of epigallocatechin gallate present in about 1 to about 5 cups of green tea.

11. The dietary supplement of claim 1 wherein the phytonutrients are incorporated into a supplemental food product.

12. A dietary supplement comprising:
a plurality of phytonutrients including,
lutein in an amount of about 1.9 mg to about 20 mg;
lycopene in an amount of about 3 mg to about 20 mg;

quercetin in an amount of about 90 mg to about 150 mg;
ellagic acid in an amount of about 20 mg to about 150 mg;
hesperidin in an amount of about 15 mg to about 225 mg; and
epigallocatechin gallate in an amount of about 25 mg to about 150 mg,
wherein the dietary supplement corrects a dietary deficiency of each of the phytonutrients in a subject, wherein the combination of phytonutrients provides an oxygen radical absorption of at least 3000.

* * * * *